United States Patent [19]

Behner et al.

[11] Patent Number: 5,234,935
[45] Date of Patent: Aug. 10, 1993

[54] N-ALKYLATED 1,4-DIHYDROPYRIDINE-DICARBOXYLIC ACID ESTERS

[75] Inventors: Otto Behner; Hartmut Wollweber, both of Wuppertal; Bruno Rosen, Wülfrath; Siegfried Zaiss; Siegfried Goldmann, both of Wuppertal, all of Fed. Rep. of Germany

[73] Assignee: Bayer Aktiengesellschaft, Leverkusen, Fed. Rep. of Germany

[21] Appl. No.: 680,454

[22] Filed: Apr. 4, 1991

[30] Foreign Application Priority Data

Apr. 11, 1990 [DE] Fed. Rep. of Germany ....... 4011695

[51] Int. Cl.$^5$ ................. C07D 211/86; A61K 31/455
[52] U.S. Cl. ..................................... 514/356; 546/321
[58] Field of Search ........................ 546/321; 514/356

[56] References Cited

U.S. PATENT DOCUMENTS

| | | | |
|---|---|---|---|
| 3,787,444 | 1/1974 | Gosteli | 549/12 |
| 3,883,543 | 5/1975 | Bossert | 546/321 |
| 3,956,341 | 5/1976 | Loev | 546/321 |
| 3,956,395 | 5/1976 | Meyer | 568/34 |
| 4,707,486 | 11/1987 | Flockerzi et al. | 514/318 |
| 4,780,538 | 10/1988 | Pitzenberger | 546/321 |
| 4,975,440 | 12/1990 | Flockerzi et al. | 514/318 |

FOREIGN PATENT DOCUMENTS

| | | |
|---|---|---|
| 1813436 | 10/1970 | Fed. Rep. of Germany . |
| 1923990 | 11/1970 | Fed. Rep. of Germany . |
| 1963188 | 6/1971 | Fed. Rep. of Germany . |
| 2210667 | 3/1972 | Fed. Rep. of Germany . |
| 2228377 | 6/1972 | Fed. Rep. of Germany . |
| 2210672 | 9/1973 | Fed. Rep. of Germany . |
| 2015516 | 9/1979 | United Kingdom . |
| 2192132 | 1/1988 | United Kingdom . |

OTHER PUBLICATIONS

Thomas D. Harris, "Ortho Lithiation via a Carbonyl Synthon," J. Org. Chem., vol. 44, No. 12, 1979, pp. 2004–2007.

"Meldrum's Acid in Organic Synthesis 2. A General and Versatile Synthesis of β-Keto Esters," in J. Org. Chem., vol. 43, No. 10, 1978, pp. 2087–2088.

Wesley J. Dale, "The Anomalous Reaction of Methylmagnesium Iodide with the Tosylate of p-Hydroxybenzaldehyde," in J. Am. Chem. Soc. 78, 1956, pp. 2543–2547.

(List continued on next page.)

Primary Examiner—Jane T. Fan
Attorney, Agent, or Firm—Sprung Horn Kramer & Woods

[57] ABSTRACT

Improving circulation, with minimal effect on blood pressure, using N-alkylated 1,4-dihydropyridines of the formula

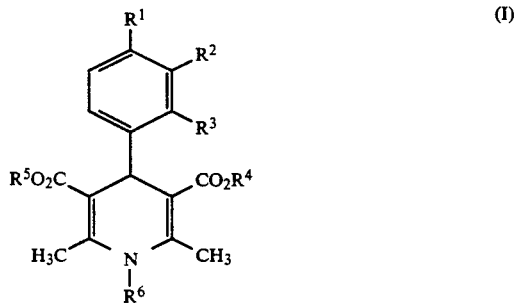

(I)

in which
$R^1$ represents hydrogen, nitro, cyano, trifluoromethyl, trifluoromethoxy, halogen or methyl,
$R^2$ represents hydrogen, halogen, nitro, hydroxyl, trifluoromethyl or methyl,
$R^3$ represents hydrogen or cyano, or
$R^2$ and $R^3$ together form a fused benzo ring,
$R^4$ and $R^5$ are identical or different and represent straight-chain or branched alkyl having up to 8 carbon atoms, which is optionally substituted by alkoxy having up to 4 carbon atoms, and
$R^6$ represents straight-chain or branched alkyl having up to 10 carbon atoms or represents cycloalkyl having 3 to 7 carbon atoms.

Many of the compounds are new.

9 Claims, No Drawings

OTHER PUBLICATIONS

Samuel A. Glickman, "Structure of β-Amino Derivatives of α,β-Unsaturated Lactones and Esters," *J. Am. Chem.* 67, 1945, pp. 1017–1020.

Houben Weyl's Methods of Organic Chemistry, vol. VII/4, 1968, p. 230.

Alfred Dornow, "Uber Einige Umsetzungen des Nitroacetons," in Liebig's Ann. Chem. 602, 1957, pp. 14–23.

Loev et al. CA 81:145644∇.

Vitolina et al. CA 101:16792z.

Meyer et al. CA 79:146412p, 79:146410m.

Bossert CA 80-14958.

Ogle et al. CA 101:90153h.

N-ALKYLATED 1,4-DIHYDROPYRIDINE-DICARBOXYLIC ACID ESTERS

The present invention relates to the use of N-alkylated 1,4-dihydropyridinedicarboxylic acid esters, some of which are known, as haemorheological medicaments, new active compounds and processes for their preparation, in particular their use as medicaments in acute and chronic ischaemic disorders which are associated with microcirculation disorders. This action can occur both in the peripheral and in the cerebral vascular system.

It is known that 1,4-dihydropyridinedicarboxylic acid esters have a calcium antagonist or calcium agonist action, and can thus be employed as circulation-influencing agents [compare DOS (German Offenlegungsschrift) 2,506,987; DE 2,210,667].

EP 240,828 describes hypotensive 1,4-dihydropyridines having haemorheological properties.

The use of hypotensive 1,4-dihydropyridines substituted by heterocycles as haemorheological agents has also been published in DE 3,720,509.

It has now been found that the N-alkylated 1,4-dihydropyridinedicarboxylic acid esters, some of which are known and some of which are new, of the general formula (I)

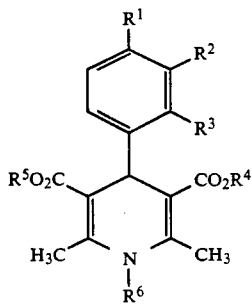

in which $R^1$ represents hydrogen, nitro, cyano, trifluoromethyl, trifluoromethoxy, halogen or methyl, $R^2$ represents hydrogen, halogen, nitro, hydroxyl, trifluoromethyl or methyl, $R^3$ represents hydrogen or cyano, or $R^2$ and $R^3$ together form a fused benzo ring, $R^4$ and $R^5$ are identical or different and represent straight-chain or branched alkyl having up to 8 carbon atoms, which is optionally substituted by alkoxy having up to 4 carbon atoms, and $R^6$ represents straight-chain or branched alkyl having up to 10 carbon atoms or represents cycloalkyl having 3 to 7 carbon atoms, surprisingly have a strong haemorheological action combined with neutral blood pressure behavior and improve the circulation, in particular the microcirculation, and are thus suitable for use in the control of acute and chronic ischaemic disorders.

Compounds of the general formula (I) in which $R^1$ represents hydrogen, nitro, trifluoromethyl, trifluoromethoxy, cyano, fluorine, chlorine, bromine or methyl, $R^2$ represents hydrogen, fluorine, chlorine, bromine, nitro, hydroxyl, trifluoromethyl or methyl, $R^3$ represents hydrogen or cyano, or $R^2$ and $R^3$ together form a fused benzo ring, $R^4$ and $R^5$ are identical or different and represent straight-chain or branched alkyl having up to 8 carbon atoms, which is optionally substituted by methoxy and $R^6$ represents straight-chain or branched alkyl having up to 4 carbon atoms, or cyclopropyl, are preferred for the control of acute and chronic ischaemic disorders.

Compounds of the general formula (I) in which $R^1$ represents hydrogen, nitro, trifluoromethyl, trifluoromethoxy, cyano, fluorine, bromine, chlorine or methyl, $R^2$ represents hydrogen, fluorine, chlorine, nitro, hydroxyl, trifluoromethyl or methyl, $R^3$ represents hydrogen or cyano, or $R^2$ and $R^3$ together form a fused benzo ring, $R^4$ and $R^5$ are identical or different and represent straight-chain or branched alkyl having up to 6 carbon atoms, which is optionally substituted by methoxy, and $R^6$ represents methyl, ethyl or cyclopropyl, are particularly preferred for the control of acute and chronic ischaemic disorders.

The compounds according to the invention show an unforeseeable, useful pharmacological action spectrum.

Combined with a neutral blood pressure behavior a dose range up to at least 10 mg/kg i.v. and 30 mg/kg p.o., they increase the circulation, in particular the microcirculation, by influencing the deformability of erythrocytes and also the inhibition of the activation and adhesion of leukocytes.

The blood pressure neutrality is determined in the following models, which are typical for dihydropyridines: in SH rats after p.o. administration by measurement in the tail artery (Riva Rocci method) and in anaesthetized Wistar rats after i.v. administration (via a catheter inserted in the carotid artery). Blood-neutral compounds are designated as those which reduce the blood pressure by at most 20% of the starting value in both test models at the dose indicated. The difference between the therapeutic dose and the blood pressure action occurring is at least a factor of 10, as a rule a factor of $\geq 30$, in particular $\geq 100$.

They can therefore be employed for the production of medicaments for the treatment of acute and chronic ischaemic disorders, such as intermittent claudication, myocardial infarct, cerebral infarct and also reperfusion damage and shock.

The invention additionally relates to new 1,4-dihydropyridinedicarboxylic acid esters which are listed below:

dibutyl 1,2,6-trimethyl-4-(1-naphthyl)-1,4-dihydropyridine-3,5-dicarboxylate diethyl 1,2,6-trimethyl-4-(4-fluorophenyl)-1,4-dihydropyridine-3,5-dicarboxylate dipropyl 1,2,6-trimethyl-4-(2-cyanophenyl)-1,4-dihydropyridine- 3,5-dicarboxylate dibutyl 1,2,6-trimethyl-4-(4-nitrophenyl)-1,4-dihydropyridine-3,5-dicarboxylate dimethyl 1,2,6-trimethyl-4-(4-trifluoromethylphenyl)-1,4-dihydro-pyridine-3,5-dicarboxylate methyl propyl 1,2,6-trimethyl-4-(4-trifluoromethylphenyl)-1,4-dihydro-pyridine-3,5-dicarboxylate methyl isopropyl 1,2,6-trimethyl-4-(4-trifluoromethylphenyl)-1,4-dihydro-pyridine-3,5-dicarboxylate methyl 1,2-dimethylpropyl 2,6-trimethyl-4-(4-trifluoromethylphenyl)-1,4-dihydro-pyridine-3,5-dicarboxylate methyl 2-methoxyethyl 1,2,6-trimethyl-4-(4-trifluoromethylphenyl)-1,4-dihydro-pyridine-3,5-dicarboxylate dimethyl 1,2,6-trimethyl-4-(3-fluorophenyl)-1,4-dihydropyridine-3,5-dicarboxylate dipropyl 1,2,6-trimethyl-4-(3-methylphenyl)-1,4-dihydropyridine-3,5-dicarboxylate dimethyl 1,2,6-trimethyl-4-(4-bromophenyl)-1,4-dihydropyridine-3,5-dicarboxylate dipropyl 1,2,6-trimethyl-4-(4-bromophenyl)-1,4-dihydropyridine-3,5-dicarboxylate dibutyl 1,2,6-trimethyl-4-(4-bromophenyl)-1,4-dihydropyridine-3,5-dicarboxylate dipropyl 1,2,6-trimethyl-4-(4-cyanophenyl)-1,4-dihydropyridine-3,5-dicarboxylate diethyl 1-cyclopropyl-2,6-dimethyl-4-(3-trifluoromethylphenyl)-1,4-dihydro-pyridine-3,5-dicarboxylate dimethyl 1-ethyl-2,6-dimethyl-4-(4-trifluoromethylphenyl)-1,4-dihydro-pyridine-3,5-dicarboxylate dimethyl 1-cyclopropyl-2,6-dimethyl-4-(4-trifluoromethylphenyl)- 1,4-dihydro-pyridine-3,5-dicarboxylate diethyl 1-cyclopropyl-2,6-dimethyl-4-(4-trifluoromethylphenyl)-1,4-dihydro-pyridine-3,5-dicarboxylate diisopropyl 1,2,6-trimethyl-4-(4-trifluoromethylphenyl)-1,4-dihydro-pyridine-3,5-dicarboxylate dimethyl 1,2,6-trimethyl-4-(4-methyl-3-nitrophenyl)-1,4-dihydro-pyridine-3,5-dicarboxylate dipropyl 1,2,6-trimethyl-4-(4-methyl-3-nitrophenyl)-1,4-dihydro-pyridine-3,5-dicarboxylate dibutyl 1,2,6-trimethyl-4-(4-methyl-3-nitrophenyl)-1,4-dihydro-pyridine-3,5-dicarboxylate diethyl 1,2,6-trimethyl-4-(4-methyl-3-nitrophenyl)-1,4-dihydro-pyridine-3,5-dicarboxylate diethyl 1,2,6-trimethyl-4-(3-chloro-4-nitrophenyl)-1,4-dihydro-pyridine-3,5-dicarboxylate dimethyl 1,2,6-trimethyl-4-(4-chloro-3-trifluoromethylphenyl)-1,4-dihydro-pyridine-3,5-dicarboxylate dimethyl 1,2,6-trimethyl-4-(4-methyl-3-trifluoromethylphenyl)-1,4-dihydro-pyridine-3,5-dicarboxylate dimethyl 1,2,6-trimethyl-4-(3-hydroxy-4-nitrophenyl)-1,4-dihydro-pyridine-3,5-dicarboxylate dimethyl 1-cyclopropyl-2,6-dimethyl-4-(4-trifluoromethoxyphenyl)-1,4-dihydro-pyridine-3,5-dicarboxylate diethyl 1-cyclopropyl-2,6-dimethyl-4-(4-trifluoromethoxyphenyl)-1,4-dihydro-pyridine-3,5-dicarboxylate isopropyl 2-methoxyethyl 1,2,6-trimethyl-4-(4-trifluoromethylphenyl)-1,4-dihydro-pyridine-3,5-dicarboxylate diethyl 1,2,6-trimethyl-4-(4-trifluoromethylphenyl)-1,4-dihydro-pyridine-3,5-dicarboxylate methyl ethyl 1-cyclopropyl-2,6-dimethyl-4-(4-trifluoromethylphenyl)- 1,4-dihydro-pyridine-3,5-dicarboxylate propyl 2-methoxyethyl 1-cyclopropyl-2,6-dimethyl-4-(4-trifluoromethylphenyl)-1,4-dihydro-pyridine-3,5-dicarboxylate isopropyl 2-methoxyethyl 1-cyclopropyl-2,6-dimethyl-4-(4-trifluoromethylphenyl)-1,4-dihydro-pyridine-3,5-dicarboxylate diethyl 1-cyclopropyl-2,6-dimethyl-4-(4-fluorophenyl)-1,4-dihydro-pyridine-3,5-dicarboxylate dimethyl 1-cyclopropyl-2,6-dimethyl-4-(4-fluorophenyl)-1,4-dihydro-pyridine-3,5-dicarboxylate propyl butyl 1-cyclopropyl-2,6-dimethyl-4-(4-trifluorophenyl)-1,4-dihydro-pyridine-3,5-dicarboxylate butyl methyl 1-cyclopropyl-2,6-dimethyl-4-(4-trifluoromethylphenyl)-1,4-dihydro-pyridine-3,5-dicarboxylate ethyl propyl 1-cyclopropyl-2,6-dimethyl-4-(4-trifluoromethylphenyl)-1,4-dihydro-pyridine-3,5-dicarboxylate butyl ethyl 1-cyclopropyl-2,6-dimethyl-4-(4-trifluoromethylphenyl)-1,4-dihydro-pyridine-3,5-dicarboxylate ethyl isopropyl 1-cyclopropyl-2,6-dimethyl-4-(4-trifluoromethylphenyl)-1,4-dihydro-pyridine-3,5-dicarboxylate.

Particularly preferred compounds are the 1,4-dihydropyridinedicarboxylic acid esters whose phenyl ring is monosubstituted in the para-position by fluorine, bromine or by the CF: group.

Very particularly preferred compounds are the following:

dimethyl 1,2,6-trimethyl-4-(4-bromophenyl)-1,4-dihydropyridine-3,5-dicarboxylate (Ex 13) diethyl 1-cyclopropyl-2,6-dimethyl-4-(4-trifluoromethylphenyl)-1,4-dihydro-pyridine-3,5-dicarboxylate (Ex 19) dimethyl 1-cyclopropyl-2,6-dimethyl-4-(4-trifluoromethylphenyl)-1,4-dihydro-pyridine-3,5-dicarboxylate (Ex 18) dimethyl 1,2,6-trimethyl-4-(4-trifluoromethylphenyl)-1,4-dihydro-pyridine-3,5-dicarboxylate (Ex 3)

methyl 1,2-dimethylpropyl 1,2,6-trimethyl-4-(4-trifluoromethylphenyl)-1,4-dihydro-pyridine-3,5-dicarboxylate Some of the compounds according to the invention exist in stereoisomeric forms which behave either as image and mirror image (enantiomers) or which do not behave as image and mirror image (diastereomers). The invention relates both to the antipodes and to the racemic forms and the diastereomer mixtures. The racemic forms can be separated into the stereoisomerically uniform components in a known manner, just like the diastereomers (compare E. L. Eliel, Stereochemistry of Carbon Compounds, McGraw Hill, 1962).

The compounds of the general formula (I) according to the invention and the new compounds can be prepared by a process in which

[A] benzylidene compounds of the general formula (II)

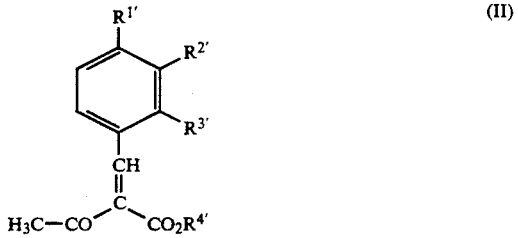

in which $R^{1'}$, $R^{2'}$, $R^{3'}$ and $R^{4'}$ have the abovementioned meaning of $R^1$, $R^2$, $R^3$ and $R^4$ and additionally include the respective scope of meaning of the new compounds listed above, are either first reacted with β-aminocrotonic acid esters of the general formula (III)

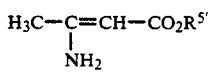 (III)

in which
R⁵' has the abovementioned meaning of R⁵ and additionally includes the scope of meaning of the new compounds listed above, in inert solvents and in a last step the NH function is alkylated by a customary method, or the compounds of the general formula (II) are directly reacted, if desired in the presence of Lewis acids such as titanium tetrachloride, with compounds of the general formula (IIIa)

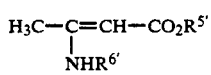 (IIIa)

in which
R⁵' has the abovementioned meaning,
R⁶' has the abovementioned meaning of R⁶ and additionally includes the scope of meaning of the new compounds listed above, or

[B] aldehydes of the general formula (IV)

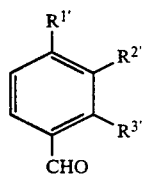 (IV)

in which
R¹', R²' and R³' have the meanings indicated under process [A], are first reacted with β-ketocarboxylic acid esters of the general formulae (V) and (Va)

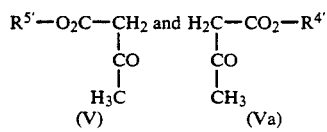

in which
R⁴'and R⁵' likewise have the meanings indicated under process [A] and then are either reacted directly with amines or the corresponding amine hydrochlorides of the general formula (VI)

 H₂N—R⁶' (VI)

in which
R⁶' has the meaning indicated above under process [A] or are first ring-closed with ammonia in organic, if appropriate inert, solvents according to a customary method and in a last step alkylated by the method mentioned above, and in the case of the enantiomerically pure esters, the enantiomerically pure carboxylic acids are first prepared and these are esterified with the appropriate alcohols by a customary method, if desired by means of a reactive acid derivative.

The process, according to the invention, for the preparation of the new compounds can be illustrated by way of example by the following equation:

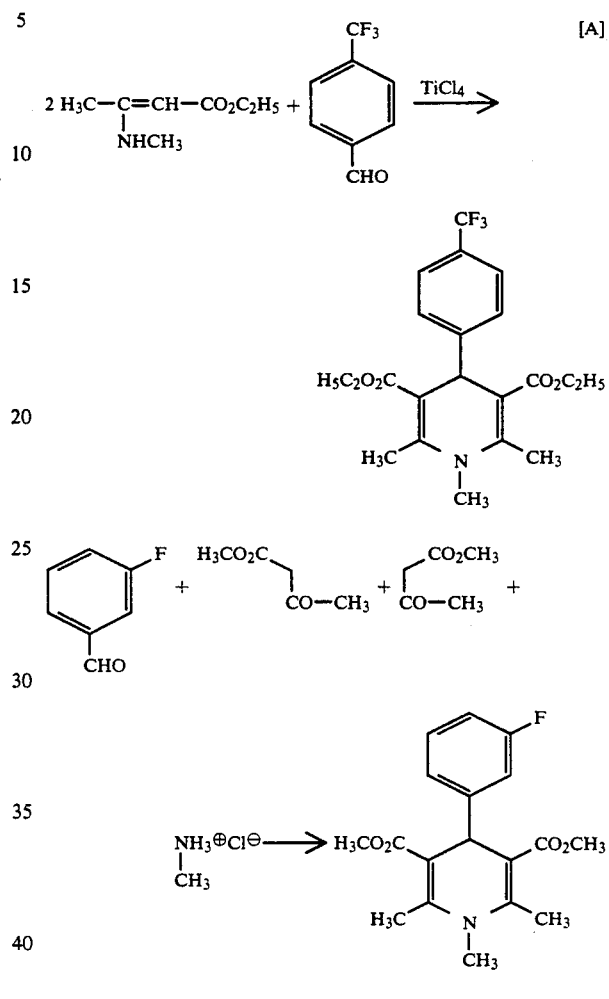

DESCRIPTION OF PROCESSES

Suitable solvents are water, or organic solvents which do not change under the reaction conditions. These preferably include alcohols such as methanol, ethanol, propanol, isopropanol, ethers such as diethyl ether, dioxane, tetrahydrofuran, glycol monomethyl ether or glycol dimethyl ether, or amides such as dimethylformamide, dimethylacetamide or hexamethylphosphoric triamide, or glacial acetic acid, dimethyl sulphoxide, acetonitrile or pyridine.

The reaction temperatures can be varied within a relatively wide range. In general, the reaction is carried out between +10° C. and +150° C., preferably between +20° C. and +100° C., in particular at the boiling point of the respective solvent.

The reaction can be carried out at normal pressure, but also at elevated or reduced pressure. In general, the reaction is carried out at normal pressure.

When carrying out process variants A and B according to the invention, any desired ratio of the substances participating in the reaction can be used. In general, however, molar amounts of the reactants are used. The isolation and purification of the substances according to the invention are preferably carried out by removing the solvent by distillation in vacuo and recrystallizing the residue, which may only be obtained in crystalline form after ice-cooling, from a suitable solvent. In some cases, it may be necessary to purify the compounds according to the invention by chromatography.

The ylidene compounds of the general formula (II) are known in some cases or can be prepared by known methods [compare H. Dornow and W. Sassenberg, Liebigs Ann. Chem. 602, 14 (1957)].

The aldehydes of the general formula (IV) employed as starting materials are known or can be prepared by known methods [DOS (German Offenlegungsschrift 2,165,260; 2,401,665; T. D. Harris, G. P. Roth, J. Org. Chem. 44, 2004 (1979); W. J. Dale, H. E. Hennis, J. Am. Chem. Soc. 78, 2543 (1956); Chem. Abstr. 59, 13929 (1963)].

The β-ketocarboxylic acid esters of the general formulae (V) and (Va) employed as starting materials are known or can be prepared by known methods [D. Borrmann in Houben Weyl's "Methoden der organischen Chemie" (Methods of Organic Chemistry) Vol. VII/4, 230 (1968); Y. Oikawa, K. Sugano, O. Yonemitsu, J. Org. Chem. 43, 2087 (1978)].

The β-aminocrotonic acid esters of the general formulae (III) and (IIIa) employed as starting materials are known or can be prepared by known methods [DOS (German Offenlegungsschrift) 2,228,377; F. A. Glickman, A. C. Cope, J. Am. Chem. Soc. 67, 1017 (1945)].

The compounds of the general formula (VI) are also known.

Examples of reactive acid derivatives which may be mentioned are: activated esters, hydroxysuccinimide esters, acid imidazolides, acid halides, mixed anhydrides or reaction in the presence of cyclohexylcarbodiimide.

Examples of alkylating agents which can be employed in the process are $(C_1-C_8)$-alkyl halides, sulphonic acid esters or substituted or unsubstituted $(C_1-C_6)$-dialkyl sulphates, preferably methyl iodide, p-toluenesulphonic acid esters or dimethyl sulphate.

The alkylation is carried out in the above-mentioned solvents at temperatures from 0° C. to +150° C., preferably at room temperature up to +100° C. at normal pressure.

Activating reagents which may be mentioned by way of example for the preparation of the reactive acid derivatives are, in addition to the inorganic halides such as thionyl chloride, phosphorus trichloride or phosphorus pentachloride, or carbonyldiimidazole, carbodiimides such as cyclohexylcarbodiimide or 1-cyclohexyl-3-[2-(N-methyl-morpholino)ethyl]carbodiimide-p-toluenesulphonate or N-hydroxyphthalimide or N-hydroxybenzotriazole in the presence of dicyclohexylcarbodiimide.

Suitable solvents for the reaction with the appropriate alcohols are the abovementioned solvents with the exception of the alcohols.

The diastereomer pairs are separated by known methods such as column chromatography, fractional crystallization or Craig partition [for Craig partition see, for example, "Verteilungsverfahren im Laboratorium" (Partition Methods in the Laboratory), E. Hecher, Verlag Chemie GmbH, Weinheim, Bergstr. (1955)].

The new and the known compounds according to the invention show an unforeseeable, useful pharmacological action spectrum.

The following in vitro and in vivo tests show the interesting actions of the compounds according to the invention.

I) Erythrocyte Function

The deformability of erythrocytes plays an essential role in the origin and course of acute or chronic ischaemic disorders. It determines the viscosity of the blood and thus its distribution in the microcirculation. The tests used detect various determinants:

Test a) measures the calcium permeability ($^{45}$Ca) by blockade of the ATPases by Na ortho-vanadate. As a result, calcium can accumulate in the erythrocytes. A consequence is a reduced flexibility. $ED_{50}$ values (mol/l) for the inhibition of calcium influx are given for test a).

Test b) detects the antihaemolytic action of the substances ($ED_{50}$, mol/l). In this test, calcium-laden erythrocytes are forced through small pores under high shearing stresses, so that haemoglobin is released as a result of their haemolysis and measured. The reduction in haemoglobin release is the measured quantity.

Test c) detects the filterability of calcium-laden erythrocytes through 5 μm pores ($ED_{50}$, mol/l). In this test, the membrane flexibility plays a role under small force gradients.

Test d) detects the viscosity of erythrocyte suspensions in glass capillaries (25 μm diameter) at low shearing stresses occurring in areas of vessels behind a stenosis. As a result of increasing the extracellular calcium, the viscosity increases.

The table gives the percentage improvement in the viscosity relative to damage=100% at a test dose of 10 ng/ml.

a) Calcium Permeability of Erythrocytes

After blockade of the membrane-immobilized ATPases by Na ortho-vanadate (0.75 mM), the calcium permeability is measured ($^{45}$Ca method). Accumulation of calcium reduces the flexibility of the erythrocytes.

TABLE I

| Example No. | $ED_{50}$ of the inhibition (mol/l) |
| --- | --- |
| 3 | $5 \times 10^{-6}$ |
| 13 | $5 \times 10^{-6}$ |
| 21 | $5 \times 10^{-6}$ |
| 27 | $10^{-6}$ |

Antihaemolytic Action of Erythrocytes

Normal erythrocytes become haemolytic under high shearing stresses. The haemolysis of calcium-laden cells is particularly pronounced. This measure of mechanical stability is used for substance characterization. The measured quantity is the concentration of free haemoglobin in the medium.

TABLE II

| Example No. | $ED_{50}$ of the antihaemolytic action (mol/l) |
| --- | --- |
| 2 | $10^{-7}$ |
| 13 | $5 \times 10^{-7}$ |
| 15 | $5 \times 10^{-6}$ |
| 21 | $5 \times 10^{-7}$ |
| 22 | $5 \times 10^{-7}$ |
| 26 | $3 \times 10^{-8}$ |
| 27 | $5 \times 10^{-8}$ | c) Filtration of Erythrocytes

Filtration of erythrocytes through 5 μm sieve pores is an established method for the determination of the deformability of erythrocytes. The cells are sheared in normal buffer for 30 min so that the calcium concentration increases intracellularly and the flexibility is reduced.

TABLE III

| Ex. No. | $ED_{50}$ improvement in the flexibility compared to damage to control (mol/l) |
|---|---|
| 1 | $5 \times 10^{-6}$ |
| 3 | $5 \times 10^{-6}$ |
| 26 | $5 \times 10^{-6}$ |
| 28 | $5 \times 10^{-6}$ | d) Viscosity in Glass Capillaries

The biophysical interactions of erythrocytes relevant to the circulation can be investigated in glass capillaries (diameter 20–30 μm). The resulting viscosity depends on the condition of the cells. In the case of calcium loading, the viscosity increases. The percentage improvement in the viscosity relative to the damaged but untreated control is given at 0.7 Pa. The test dose is $10^{-8}$ g/ml.

TABLE IV

| Example No. | Effect (%) |
|---|---|
| 3 | 143 |
| 13 | 120 |
| 14 | 206 |
| 15 | 75 |
| 17 | 62 |
| 18 | 208 |
| 24 | 226 |

II) Leukocyte Function

The microcirculation can be directly observed in the hamster cheek pouch model. Measured quantities are leukocyte adhesion and also vessel diameter and erythrocyte velocity. The adhesion was quantified under ischaemic and non-ischaemic experimental conditions. Under non-ischaemic conditions, the adhesion is quantified in the area of small venules, under ischaemic conditions (10 min circulation stop) the adhesion is quantified in small arterioles. The results of the control experiments are given relative to 100%. 0.1 mg/kg i.v. is in each case chosen as the test dose, the results are decreases in % of the control.

TABLE V

| Example No. | Non-ischaemic control = 100% | Ischaemic control = 100% |
|---|---|---|
| 3 | 63% | 31% |
| 6 | 50% | 56% |
| 9 | 70% | 36% |
| 18 | 54% | 32% |
| 19 | 61% | 34% |

III) Blood Pressure

The clinical state of knowledge shows that anti-ischaemic actions of dihydropyridines are frequently masked by vasodilatation. It was therefore the aim to find blood pressure-inactive DHPs (i.e. difference between haemorheological action and blood pressure-reducing action $\geq 10$). The following table shows the doses at which a blood pressure reduction occurs in the case of p.o. administration (SH rats) or i.v. administration (anaesthetized Wistar rats).

TABLE VI

| Example No. | p.o. (mg/kg) | i.v. (mg/kg) |
|---|---|---|
| 3 | >30 | >10 |
| 6 | >30 | >10 |
| 9 | >30 | >10 |
| 18 | >30 | >10 |
| 19 | >100 | >10 |

The table shows that, in comparison to model II the difference between the therapeutic action and blood pressure action (i.v.) is at least 100.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this connection, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, in the case of the use of water as a diluent, organic solvents can optionally be used as auxiliary solvents.

Administration is carried out in a customary manner, preferably orally or parenterally, in particular perlingually or intravenously.

In the case of parenteral use, solutions of the active compounds using suitable liquid excipient materials can be employed.

In general it has proved advantageous on intravenous administration to administer amounts of about 0.001 to 1 mg/kg, preferably about 0.01 to 0.5 mg/kg of body weight to achieve effective results, and on oral administration the dosage is about 0.01 to 20 mg/kg, preferably 0.1 to 10 mg/kg of body weight.

In spite of this, it may be necessary to deviate from the amounts mentioned, in particular depending on the body weight or the type of administration route, on individual behavior towards the medicament, the nature of its formulation and the point in time or interval at which administration takes place. Thus, in some cases it may be sufficient to manage with less than the above-mentioned minimum amount, while in other cases the upper limit mentioned must be exceeded. In the case of the administration of larger amounts, it may be advisable to divide these into several individual doses over the course of the day.

PREPARATION EXAMPLES

Example 1

Diethyl 1,2,6-trimethyl-4-(4-fluorophenyl)-1,4-dihydropyridine-3,5-dicarboxylate

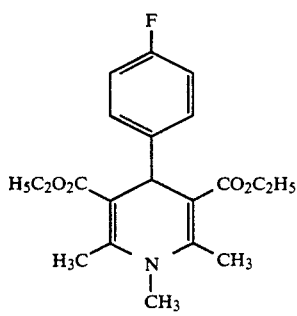

2.78 g (0.008 mol) of diethyl 2,6-dimethyl-4-(4-fluorophenyl)-1,4-dihydro-pyridine-3,5-dicarboxylate dissolved in 25 ml of 1,2-dimethoxyethane, and 0.30 g (0.01 mol) of 80% strength sodium hydride and, after 30 min, 1.43 g (0.01 mol) of methyl iodide are added. The mixture is stirred at room temperature for 3 hours, neutralized with dilute hydrochloric acid and evaporated in vacuo. The residue is purified by chromatography on silica gel (methylene chloride).

Yield: 1.85 g (63.9% of theory).

Melting point: 90°–92° C.

Example 2

Dimethyl 4-(3-fluorophenyl)-1,2,6-trimethyl-1,4-dihydropyridine-3,5-dicarboxylate

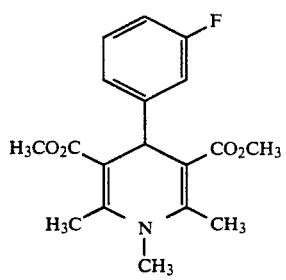

A mixture of 3.84 g (0.03 mol) of 3-fluorobenzaldehyde, 7.04 g (0.06 mol) of methyl acetoacetate and 2.07 g (0.03 mol) of methylamine hydrochloride in 20 ml of pyridine is stirred under reflux for 5 hours. After removing the pyridine by distillation, the mixture is partitioned between water and methylene chloride, and the organic phase is washed with water, dried over sodium sulphate and evaporated. The residue is recrystallized from methanol.

Melting point: 117°–118° C.

Yield: 6.14 g (61.4% of theory)

Example 3

Dimethyl 1,2,6-trimethyl-4-(4-trifluoromethylphenyl)-1,4-dihydro-pyridine-3,5-dicarboxylate

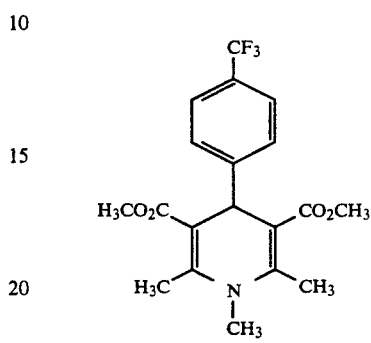

A mixture of 5.22 g (0.03 mol) of 4-trifluoromethylbenzaldehyde, 7.04 g (0.06 mol) of methyl acetoacetate and 2.07 g (0.03 mol) of methylamine hydrochloride in 20 ml of pyridine is stirred under reflux for 5 hours. After removing the pyridine by distillation, the mixture is partitioned between water and methylene chloride, and the organic phase is washed with water, dried over sodium sulphate and evaporated. The residue is recrystallized from methanol.

Melting point: 154°–155° C.

Yield: 7.88 g (68.5% of theory)

The examples shown in Tables 1 and 2 were prepared in analogy to the procedure of Example 3.

TABLE 1

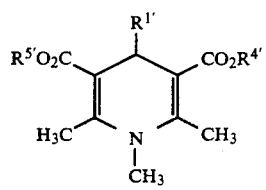

| Example No. | $R^{1'}$ | $R^{4'}$ | $R^{5'}$ | m.p. °C. | Yield (% of theory) |
|---|---|---|---|---|---|
| 4 | 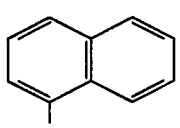 | —$C_2H_5$ | —$C_2H_5$ | 90–92 | 63.9 |

TABLE 2

[Structure: 1,4-dihydropyridine with R1' at para position of phenyl, R3' at ortho; 3-CO2R4', 5-CO2R5'; N-CH3; 2,6-dimethyl]

| Ex. No. | R1' | R3' | R4' | R5' | m.p. °C. | Yield (% of theory) |
|---|---|---|---|---|---|---|
| 5 | H | CN | —C3H7 | —C3H7 | Oil | 19.4 |
| 6 | NO2 | H | —C4H9 | —C4H9 | 81–84 | 62.7 |
| 7 | CF3 | H | —C3H7 | —CH3 | 76–78 | |
| 8 | CF3 | H | —CH(CH3)2 | —CH3 | 86–88 | |
| 9 | CF3 | H | —CH—CH(CH3)2<br>\|<br>CH3 | —CH3 | 54–57 | |
| 10 | CF3 | H | —(CH2)2—OCH3 | —CH3 | 71–73 | |

Example 11

Dipropyl 4-(4-bromophenyl)-1,2,6-trimethyl-1,4-dihydropyridine-3,5-dicarboxylate

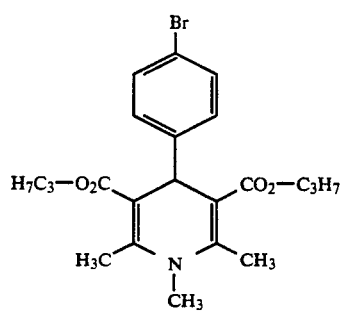

A solution of 6.22 g (0.02 mol) of propyl 2-(4-bromobenzylidene)acetoacetate and 3.14 g (0.02 mol) of propyl 3-methylamino-crotonate in 25 ml of 2-butanol is stirred under reflux for 10 hours. The mixture is then concentrated in vacuo, and the precipitate formed in the cold is filtered off with suction. After recrystallization from propanol, 5.32 g (59.1% of theory) of melting point 97°–99° C. are obtained.

The compounds shown in Table 3 can be prepared analogously to Example 11.

TABLE 3

[Structure: 1,4-dihydropyridine with R1' para and R2' meta on phenyl; 3-CO2R4', 5-CO2R5'; N-R6'; 2,6-dimethyl]

| Ex. No. | R1' | R2' | R4' | R5' | R6' | m.p. °C. | Yield (% of theory) |
|---|---|---|---|---|---|---|---|
| 12 | H | —CH3 | —C3H7 | —C3H7 | —CH3 | 67–68 | 23.3 |
| 13 | —Br | H | —CH3 | —CH3 | —CH3 | 163–167 | 59.5 |
| 14 | —Br | H | —C4H9 | —C4H9 | —CH3 | 66–68 | 36.5 |
| 15 | —CN | H | —C3H7 | —C3H7 | —CH3 | 116–119 | 45.7 |
| 16 | H | —CF3 | —C2H5 | —C2H5 | △ | 112–114 | 22.4 |
| 17 | —CF3 | H | —CH3 | —CH3 | —C2H5 | 119–129 | 15.5 |
| 18 | —CF3 | H | —CH3 | —CH3 | △ | 137–138 | 15.6 |
| 19 | —CF3 | H | —C2H5 | —C2H5 | △ | 111–113 | 15.5 |
| 20 | —CF3 | H | —CH(CH3)2 | —CH(CH3)2 | —CH3 | 106–108 | 49.1 |
| 21 | —CH3 | —NO2 | —CH3 | —CH3 | —CH3 | 116–118 | 66.1 |
| 22 | —CH3 | —NO2 | —C2H5 | —C2H5 | —CH3 | 97–98 | 60.1 |
| 23 | —CH3 | —NO2 | —C3H7 | —C3H7 | —CH3 | 94–96 | 41.3 |
| 24 | —CH3 | —NO2 | —C4H9 | —C4H9 | —CH3 | 89–90 | 45.4 |
| 25 | —NO2 | Cl | —C2H5 | —C2H5 | —CH3 | 128–130 | 60.1 |
| 26 | —Cl | —CF3 | —CH3 | —CH3 | —CH3 | 122–124 | 63.8 |

TABLE 3-continued

| Ex. No. | R1' | R2' | R4' | R5' | R6' | m.p. °C. | Yield (% of theory) |
|---|---|---|---|---|---|---|---|
| 27 | —CH3 | —CF3 | —CH3 | —CH3 | —CH3 | 103–105 | 4.83 |
| 28 | —NO2 | —OH | —CH3 | —CH3 | —CH3 | 187–189 | 62.6 |
| 29 | —OCF3 | H | —CH3 | —CH3 | △ | 77–78 | 13.2 |
| 30 | —OCF3 | H | —C2H5 | —C2H5 | △ | 108–109 | 18.5 |
| 31 | —CF3 | H | —CH2—CH2—OCH3 | —CH(CH3)2 | —CH3 | Oil | 74.3 |
| 31a | (+)-Enantiomer [α]589[20] 10.3 (C = 1 in CHCl3) | | | | | | |
| 31b | (−)-Enantiomer [α]589[20] −10.1 (C = 1 in CHCl3) | | | | | | |

Example 32

Diethyl 1,2,6-trimethyl-4-(4-trifluoromethylphenyl)-1,4-dihydro-pyridine-3,5-dicarboxylate

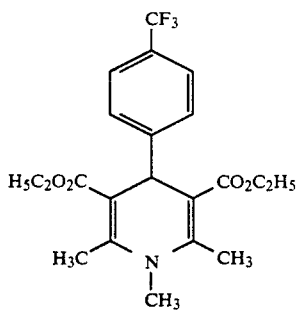

0.55 ml (5 mmol) of titanium tetrachloride, then 1 ml (10 mmol) of piperidine are added under nitrogen protection to 20 ml of toluene and the mixture is stirred for 5 min. After the dropwise addition of 2.9 g (20 mmol) of methyl 3-methylaminocrotonate, 1.36 ml (10 mmol) of 4-trifluoromethylphenylbenzaldehyde are added and the mixture is stirred at room temperature for 3 hours. For working up, 100 ml of 5% strength hydrochloric acid are added and the organic phase is taken up with ethyl acetate, and the ethyl acetate solution is washed successively with 5% hydrochloric acid and with sodium bicarbonate solution. After drying the ethyl acetate solution over sodium sulphate, evaporating and stirring the residue in n-heptane, 1.7 g (41.4% of theory) are obtained.

Melting point: 98° C.

Example 33

Methyl ethyl 1-cyclopropyl-2,6-dimethyl-4-(4-trifluoromethylphenyl)-1,4-dihydro-pyridine-3,5-dicarboxylate

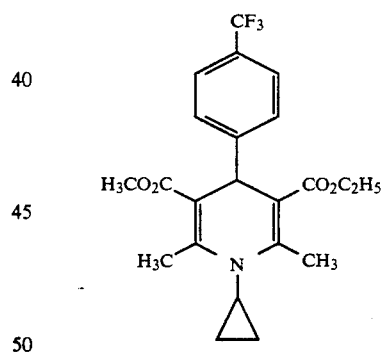

3.6 g (0.039 mol) of cyclopropylamine hydrochloride are added to a solution of 3.9 g (0.03 mol) of ethyl acetoacetate and 8.16 g (0.03 mol) of methyl 2-(4-trifluoromethylbenzylidene)acetoacetate in 50 ml of pyridine and the mixture is heated under reflux for 5 hours. The reaction product is concentrated in vacuo, the residue is taken up in methylene chloride and water, the aqueous phase is separated off, and the methylene chloride solution is dried over sodium sulphate and evaporated. The residue is purified by chromatography on silica gel using methylene chloride as the solvent. After dissolving and crystallizing the product from n-heptane, 2.2 g (17.3% of theory) are obtained. Melting point: 110° C.

The compounds shown in Table 4 can be prepared in analogy to the procedure of Examples 32 and 33.

TABLE 4

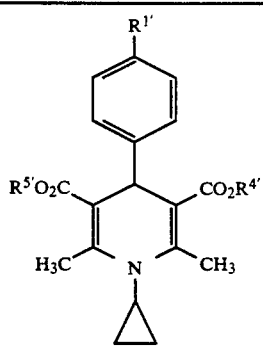

| Ex. No. | $R^{1'}$ | $R^{4'}$ | $R^{5'}$ | m.p. °C. |
|---|---|---|---|---|
| 34 | —$CF_3$ | —$C_4H_9$ | —$C_3H_7$ | 62 |
| 35 | —$CF_3$ | —$(CH_2)_2OCH_3$ | —$C_3H_7$ | Oil |
| 36 | —F | —$CH_3$ | —$CH_3$ | 140 |
| 37 | —F | —$C_2H_5$ | —$C_2H_5$ | 79 |
| 38 | —$CF_3$ | —$C_4H_9$ | —$CH_3$ | Oil |
| 39 | —$CF_3$ | —$C_3H_7$ | —$C_2H_5$ | 55–57 |
| 40 | —$CF_3$ | —$C_4H_9$ | —$C_2H_5$ | 55–60 |
| 41 | —$CF_3$ | —$C_2H_5$ | —$CH(CH_3)_2$ | 96 |

The examples shown in Table 5 were prepared in analogy to the procedures of Examples 1, 3 and 11.

TABLE 5

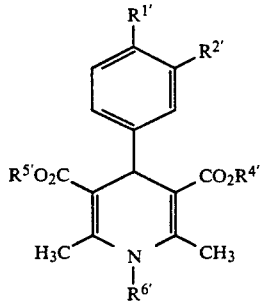

| Example No. | $R^{1'}$ | $R^{2'}$ | $R^{4'}$ | $R^{5'}$ | $R^{6'}$ | m.p. °C. | Yield (% of theory) |
|---|---|---|---|---|---|---|---|
| 42 | —$CF_3$ | H | —$CH_3$ | —$C_2H_5$ | —$CH_3$ | 116–118 | 78 |
| 43 | —F | H | —$CH_3$ | —$CH(CH_3)_2$ | —$CH_3$ | 92–94 | 73 |
| 44 | —F | H | $C_2H_5$ | —$CH(CH_3)_2$ | —$CH_3$ | Oil | 73 |
| 45 | —$CF_3$ | H | —$(CH_2)_2OCH_3$ | —$C_2H_5$ | —$CH_3$ | 56–57 | 57 |
| 46 | —$CF_3$ | H | —$(CH_2)_2OCH_3$ | $CH_2$—$CH(CH_3)_2$ | —$CH_3$ | 55–60 | 68 |
| 47 | —F | —$CF_3$ | —$CH_3$ | —$CH_3$ | —$CH_3$ | 133 | 59 |
| 48 | —F | —$CF_3$ | —$C_2H_5$ | —$C_2H_5$ | cyclopropyl | 61 | 19 |
| 49 | —$CF_3$ | H | —$CH_3$ | —$CH_2$—$CH(CH_3)_2$ | —$CH_3$ | 68 | 58 |
| 50 | —$CF_3$ | H | —$C_2H_5$ | —$CH_2$—$CH(CH_3)_2$ | —$CH_3$ | 63 | 75 |
| 51 | —F | —$CF_3$ | —$CH_3$ | —$CH_3$ | cyclopropyl | 118 | 27 |
| 52 | —F | —$CF_3$ | —$C_2H_5$ | —$C_2H_5$ | —$CH_3$ | 83 | 63 |
| 53 | —$OCF_3$ | H | —$(CH_2)_2OCH_3$ | $CH_2$—$CH(CH_3)_2$ | —$CH_3$ | 62 | 21 |
| 54 | —$OCF_3$ | H | —$C_2H_5$ | —$CH_2CH(CH_3)_2$ | —$CH_3$ | 73 | 19 |
| 55 | —$CF_3$ | H | —$(CH_2)_2OCH_3$ | —$CH_2$—$CH(CH_3)_2$ | —$CH_3$ | Oil (−) enant. $\alpha 20:-11.1$ 589 ($CHCl_3$), c:0.85 | 45 |
| 56 | —CN | H | —$CH_3$ | —$CH(CH_3)_2$ | —$CH_3$ | 122 | 50 |
| 57 | —$CF_3$ | H | —$CH_2CH(CH_3)_2$ | —$CH_2CH(CH_3)_2$ | —$CH_3$ | 68 | 45 |
| 58 | —CN | H | —$C_2H_5$ | —$CH(CH_3)_2$ | —$CH_3$ | 106–107 | 50 |

TABLE 5-continued

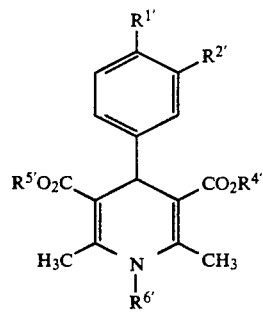

| Example No. | R¹' | R²' | R⁴' | R⁵' | R⁶' | m.p. °C. | Yield (% of theory) |
|---|---|---|---|---|---|---|---|
| 59 | $-CF_3$ | H | $-CH_2CH(CH_3)_2$ | $-CH_2CH(CH_3)_2$ | cyclopropyl | 92 | 11 |
| 60 | $-F$ | $-CF_3$ | $-(CH_2)_2OCH_3$ | $-CH(CH_3)_2$ | $-CH_3$ | 82–83 | 25 |
| 61 | $-CF_3$ | H | $-C_6H_{13}$ | $-CH_3$ | $-CH_3$ | 64–65 | 36 |
| 62 | $-CF_3$ | H | $-C_4H_9$ | $-CH_3$ | $-CH_3$ | 71–73 | 28 |
| 63 | $-CF_3$ | H | $-C_5H_{11}$ | $-CH_3$ | $-CH_3$ | 75–77 | 13 |
| 64 | $-Cl$ | H | $-CH_3$ | $-CH_3$ | $-C_2H_5$ | 143 | 21 |
| 65 | $-Cl$ | H | $-CH_3$ | $-CH_3$ | $-CH_3$ | 181 | 19 |

It will be understood that the specification and examples are illustrative but not limitative of the present invention and that other embodiments within the spirit and scope of the invention will suggest themselves to those skilled in the art.

We claim:

1. An N-substituted 1,4-dihydropyridinedicarboxylic acid ester selected from the group consisting of diethyl 1,2,6-trimethyl-4-(4-fluorophenyl)-1,4-dihydropyridine-3,5-dicarboxylate,
dimethyl 1,2,6-trimethyl-4-(4-trifluoromethylphenyl)-1,4-dihydro pyridine-3,5-dicarboxylate,
methyl propyl 1,2,6-trimethyl-4-(4-trifluoromethylphenyl)-1,4-dihydro-pyridine-3,5-dicarboxylate,
methyl isopropyl 1,2,6-trimethyl-4-(4-trifluoromethylphenyl)-1,4-dihydro-pyridine-3,5-dicarboxylate,
methyl 1,2-dimethylpropyl 1,2,6-trimethyl-4-(4-trifluoromethylphenyl)-1,4-dihydro-pyridine-3,5-dicarboxylate,
methyl 2-methoxyethyl 1,2,6-trimethyl-4-(4-trifluoromethylphenyl)-1,4-dihydro-pyridine-3,5-dicarboxylate,
dimethyl 1-ethyl-2,6-dimethyl-4-(4-trifluoromethylphenyl)-1,4-dihydro-pyridine-3,5-dicarboxylate,
dimethyl 1-cyclopropyl-2,6-dimethyl-4-(4-trifluoromethylphenyl)-1,4-dihydro-pyridine-3,5-dicarboxylate,
diethyl 1-cyclopropyl-2,6-dimethyl-4-(4-trifluoromethylphenyl)-1,4-dihydro-pyridine-3,5-dicarboxylate,
diisopropyl 1,2,6-trimethyl-4-(4-trifluoromethylphenyl)-1,4-dihydro-pyridine-3,5-dicarboxylate,
isopropyl 2-methoxyethyl 1,2,6-trimethyl-4-(4-trifluoromethylphenyl)-1,4-dihydro-pyridine-3,5-dicarboxylate,
diethyl 1,2,6-trimethyl-4-(4-trifluoromethylphenyl)-1,4-dihydro-pyridine-3,5-dicarboxylate,
methyl ethyl 1-cyclopropyl-2,6-dimethyl-4-(4-trifluoromethylphenyl)-1,4-dihydro-pyridine-3,5-dicarboxylate,
propyl 2-methoxyethyl 1-cyclopropyl-2,6-dimethyl-4-(4-trifluoromethylphenyl)-1,4-dihydro-pyridine-3,5-dicarboxylate,
isopropyl 2-methoxyethyl 1-cyclopropyl-2,6-dimethyl-4-(4-trifluoromethylphenyl)-1,4-dihydro-pyridine-3,5-dicarboxylate,
diethyl 1-cyclopropyl-2,6-dimethyl -4-(4-fluorophenyl)-1,4-dihydro-pyridine-3,5-dicarboxylate,
dimethyl 1-cyclopropyl-2,6-dimethyl-4-(4-fluorophenyl)-1,4-dihydro-pyridine-3,5-dicarboxylate,
propyl butyl 1-cyclopropyl-2,6-dimethyl-4-(4-trifluoromethylphenyl)-1,4-dihydro-pyridine-3,5-dicarboxylate,
butyl methyl 1-cyclopropyl-2,6-dimethyl-4-(4-trifluoromethylphenyl)-1,4-dihydro-pyridine-3,5-dicarboxylate,
ethyl propyl 1-cyclopropyl-2,6-dimethyl-4-(4-trifluoromethylphenyl)-1,4-dihydro-pyridine-3,5-dicarboxylate,
butyl ethyl 1-cyclopropyl-2,6-dimethyl-4-(4-trifluoromethylphenyl)-1,4-dihydro-pyridine-3,5-dicarboxylate and
ethyl isopropyl 1-cyclopropyl-2,6-dimethyl-4-(4-trifluoromethylphenyl)-1,4-dihydro-pyridine-3,5-dicarboxylate.

2. A compound according to claim 1, wherein such compound is dimethyl 1,2,6-trimethyl-4-(4-trifluoromethylphenyl)-1,4-dihydro-pyridine-3,5-dicarboxylate of the formula 3. A compound according to claim 1, wherein such compound is dimethyl 4-(4-trifluoromethylphenyl)-1-ethyl-2,6-dimethyl-1,4-dihydropyridine-3,5-dicarboxylate of the formula

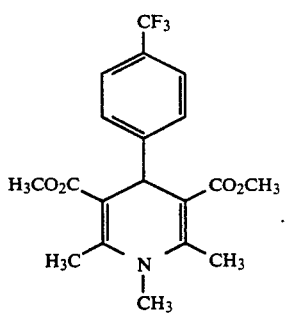

4. A compound according to claim 1, wherein such compound is dimethyl 4-(4-trifluoromethylphenyl)-1-cyclopropyl-2,6-dimethyl-1,4-dihydropyridine-3,5-dicarboxylate of the formula

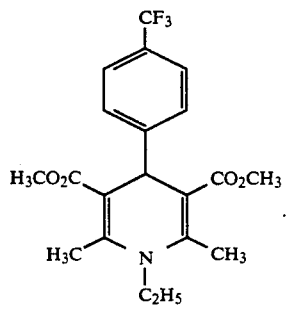

5. A compound according to claim 1, wherein such compound is diethyl 4-(4-trifluoromethylphenyl)-1-dicarboxylate of the formula

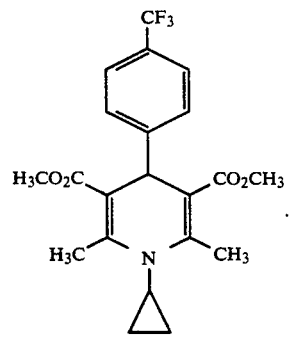

6. A compound according to claim 1, wherein such compound is methyl 1,2-dimethylpropyl 1,2,6-trimethyl-4-(4-trifluoromethylphenyl)-1,4-dihydro-pyridine-3,5-dicarboxylate.

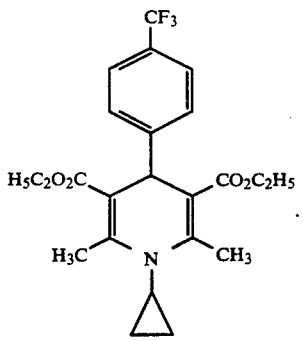

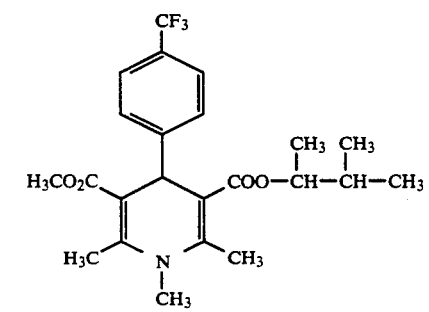

7. A myocardial infarct-preventing composition comprising an amount effective therefor of a compound according to claim 1 and a pharmaceutically acceptable diluent.

8. A method of treating a patient to prevent myocardial infarct which comprises administering to such patient an amount effective therefor of a compound according to claim 1.

9. The method according to claim 8, wherein such compound is
dimethyl 1,2,6-trimethyl-4-(4-trifluoromethylphenyl)-1,4-dihydro-pyridine-3,5-dicarboxylate,
dimethyl 4-(4-trifluoromethylphenyl)-1-ethyl-2,6-dimethyl-1,4-dihydropyridine-3,5-dicarboxylate,
dimethyl 4-(4-trifluoromethylphenyl)-1-cyclopropyl-2,6-dimethyl-1,4-dihydropyridine-3,5-dicarboxylate,
diethyl 4-(4-trifluoromethylphenyl)-1-cyclopropyl-2,6dimethyl-1,4-dihydropyridine-3,5-dicarboxylate, and
methyl 1,2-dimethylpropyl 1,2,6-trimethyl-4-(4-trifluoromethylphenyl)-1,4-dihydro-pyridine-3,5-dicarboxylate.

* * * * *

UNITED STATES PATENT AND TRADEMARK OFFICE
CERTIFICATE OF CORRECTION

PATENT NO. : 5,234,935
DATED : August 10, 1993
INVENTOR(S) : Behner, et al.

It is certified that error appears in the above-identified patent and that said Letters Patent is hereby corrected as shown below:

Col. 22, line 52  After " 6 " insert -- - --

Signed and Sealed this

Twenty-third Day of January, 1996

Attest:

BRUCE LEHMAN

*Attesting Officer*    Commissioner of Patents and Trademarks